United States Patent [19]

Bohn et al.

[11] 4,018,885

[45] Apr. 19, 1977

[54] STEROID-BINDING GLOBULIN AND PROCESS FOR PREPARING IT AND ANTIBODIES THERETO

[75] Inventors: Hans Bohn, Marbach near Marburg an der Lahn; Wilhelm Winckler, Wenkbach, both of Germany

[73] Assignee: Behringwerke Aktiengesellschaft, Marburg an der Lahn, Germany

[22] Filed: Oct. 24, 1974

[21] Appl. No.: 517,764

[30] Foreign Application Priority Data

Oct. 27, 1973 Germany .......................... 2353973

[52] U.S. Cl. .............................. 424/12; 23/230 B; 195/4; 260/112 R; 260/112 B; 424/85; 424/88; 424/100; 424/101; 424/105; 424/177

[51] Int. Cl.² ................ A61K 37/04; A61K 39/00; C12B 1/00; G01N 31/00

[58] Field of Search ............ 424/8, 12, 85, 88, 100, 424/101, 105, 177; 195/4; 260/112 R, 112 B

[56] References Cited

FOREIGN PATENTS OR APPLICATIONS 2,157,610  5/1973  Germany
2,148,587  4/1973  Germany
2,221,261  11/1973  Germany

OTHER PUBLICATIONS

Neurath, The Proteins, Acd. Press N. Y., vol. IV, 1966, pp. 96–101.
Bohn, Chem. Abs., vol. 80, 1974, No. 35543h.

Primary Examiner—Albert T. Meyers
Assistant Examiner—A. P. Fogelson
Attorney, Agent, or Firm—Curtis, Morris & Safford

[57] ABSTRACT

A derivative of the steroid-binding $\beta$-globulin which can be obtained therefrom by treatment with neuraminidase.

5 Claims, No Drawings

STEROID-BINDING GLOBULIN AND PROCESS FOR PREPARING IT AND ANTIBODIES THERETO

The present invention relates to a steroid-binding globulin which is a derivative of the steroid-binding β-globulin and to a process for preparing it from steroid-binding β-globulin by treatment with the enzyme neuraminidase.

It is known that among the plasma proteins designated as β-globulins a protein is present which has a particular affinity to steroid hormones and which is therefore designated as steroid-binding β-globulin or testosterone-binding globulin. It has already been proposed (c.f. DOS 2 221 261) to isolate this protein, which is also called $\beta_1$AP-glycoprotein, from placentas or from the blood of pregnant women. However, it has hitherto not been possible to obtain this β-globulin in pure form. This has the disadvantage that in the preparation of anti-serum which is directed against this protein, the impurities, even if these are present in smallest concentrations, also lead to antibody formation in the immunized animals and thereby cause unspecific side reactions of the anti-serums.

Now, we have found a derivative of the steroid-binding β-globulin which is formed by treatment of this substance with the enzyme neuraminidase and which can be prepared in very pure form. This globulin, hereinafter referred to as "steroid-binding globulin" largely corresponds in its biological properties to the original steroid-binding β-globulin and permits the preparation of anti-serums of high specificity from animals immunized with it. The steroid-binding β-globulin used as the starting material has the following properties:

a. a specific affinity to steroid hormones, b. a content of carbohydrates of 12.5 ± 3%, of which 5.7 ± 1.2% are hexoses, 3.9 ± 0.8% is hexoseamine, calculated as N-acetyl-hexoseamine, 2.9 ± 0.9% is neuraminic acid, calculated as N-acetylneuraminic acid, and 0.1 ± 0.1% is fucose, c. the capacity of being precipitated by specific anti-serums, d. an electrophoretic mobility corresponding to that of $\beta_1$-globulins, e. a sedimentation constant of 4.1 ± 1.0 S, measured in a phosphate buffer of pH 6.8, f. a sedimentation constant of 1.1 ± 0.3 S, measured in a 1% sodium dodecylsulfate solution, and g. a molecular weight of 65,000 ± 5,000.

Accordingly, the object of the present invention is a derivative of the steroid-binding β-globulins, a glycoprotein having a particular affinity to steroid hormones. The sum of all carbohydrates, hydrates of this steroid-binding globulin is 10.4 ± 2.6% (according to the method of determination by H. E. Schultze et al. (1958), Biochem. Z. 329, page 490); of these are 5.8 ± 1.2% hexoses, 4.0 ± 0.8% hexoseamine (calculated as N-acetyl-hexoseamine), 0.5 ± 0.5% neuraminic acid (calculated as N-acetylneuraminic acid) and 0.1 ± 0.1% fucose, so that, with the exception of the neuraminic acid content, the carbohydrate analysis corresponds to that for the steroid-binding β-globulin. The new globulin is precipitated by an anti-serum directed against the steroid-binding β-globulin. The electrophoretic mobility corresponds to that of a gamma-globulin. The protein of the invention dissolved in phosphate buffer of pH 6.8 has a sedimentation constant in the ultracentrifuge of 4.1 ± 1.0 S. In a 1% sodium-dodecyl-sulfate solution, the protein sediments with 1.1 ± 0.3 S. In a dodecyl-sulfate-containing polyacrylamide gel, the protein of the invention migrates in a electric tension field with the same speed as, or somewhat more rapidly than albumine, from which a molecular weight of 65,000 ± 5,000 can be deduced. After incubation of the protein before the separation in a 1% sodiumdodecylsulfate solution, a migration distance of the protein zone is measured which is comparable to that of human placenta lactogen, wherefrom a molecular weight of <20,000 can be calculated. Accordingly, a molecular structure can be assumed which comprises 4 sub-units, each of them having a molecular weight of about 16,000.

The present invention also relates to a process for preparing the steroid-binding globulin, which comprises isolating steroid-binding β-globulin from bodyfluids or tissue extracts which contain this protein in measurable concentrations, for example from human sera, preferably from the blood of pregnant women, from retroplacental serum or placental extracts, treating it with neuraminidase and purifying it in a following purification process, preferably by chromatography on an anion exchanger or by a corresponding measure, for example by electrophoresis in order to obtain a pure product.

Isolation of the steroid-binding β-globulins is effected by a selected combination of methods by which, on the one hand, the steroid-binding β-globulin is enriched and, on the other hand, this protein is separated from the plasma proteins. Without representing a limitation in any respect, the possible methods described hereinafter by way of example yield a starting material which is suitable for the preparation of the derivative of the steroid-binding β-globulin.

For this purpose, comminuted placentas are extracted with water or dilute saline solution, preferably with an about 0.5% sodium chloride solution. A pre-precipitate which does not contain the desired protein or only traces thereof is separated from the extract by the addition of an aqueous solution of a watersoluble derivative of an acridine base, advantageously diamino-ethoxy-acridine lactate which is added up to a concentration of 0.25 to 0.55, advantageously 0.4%, to the solution, at a weakly acid to neutral pH-value in the range of from pH 5 to pH 7.

Subsequently, the steroid-binding β-globulin is precipitated from the supernatant of the first precipitation in an alkaline pH-range of from pH 7 to pH 9, advantageously at pH 8.5, by adding an aqueous solution of a water-soluble derivative of an acridine base, advantageously again with diamino-ethoxy-acridinelactate, which is added to the solution up to a concentration of 0.55 to 1.1%, advantageously 0.8%. The precipitate was dissolved by suspension in water and following lowering of the pH-value with the aid of weak acids and freed from precipitant by the addition of suitable adsorbing agents, for example active charcoal and separated by centrifugation. The separation of the precipitant from the protein is effected in a particularly simple manner by suspending the precipitation in a chloride-containing aqueous solution, advantageously in an about 5% solution of sodium chloride, whereupon the precipitant precipitates and is then removed by filtration or centrifugation, while the proteins pass in solution. For further enrichment of the steroid-binding β-globulin, a precipitation with suitable salts, advantageously with ammonium sulfate is carried out in such a manner that the concentration of the salt drives out the steroid-binding globulin from the solution. In this respect, it is known that globulins are precipitated by ammonium sulfate if the latter has a saturation concentration of about 50%. After re-dissolution of the precipitate obtained by centrifugation or filtration, the solution is combined with a lower alcohol, advantageously ethanol up to a concentration at which the steroid-binding $\beta$-globulin is not yet precipitated, but a number of impurities is separated as precipitate. It has proved advantageous to add about 25% of ethanol, the addition of ethanol being effected at temperatures below room temperature, preferably at a temperature of $0° \pm 4°$ C, in order to avoid denaturation phenomena. By fractionation methods which are able to enrich within defined ranges proteins having molecular weights between 50,000 and 150,000, it is possible to further purify the steroid-binding $\beta$-globulin. Particularly suitable for such a purpose are measures of the gel-filtration, for example column chromatography using dextrane that is cross-linked with epichlorohydrine, for example Sephadex (G-150 of the firm Pharmacia, Uppsala. If desired, the gel-filtration may also be carried out after dialysis againts a dilute buffer solution, for example against a 0.01 molar trishydroxymethylaminomethane/hydrochloric acid buffer solution of pH 7.5 to 8.5, preferably pH 8.0. For the elution, there may be used, for example a 0.1 molar trishydroxymethylaminomethanehydrochloric acid buffer of pH 8, which contains, per liter, 1 M of sodium chloride. In this elution process, the steroid-binding $\beta$-globulin is eluted in the range of molecular weights of about 100,000, often directly after the 7-S-gamma-globulin of the plasma.

With utilization of the electrical properties of the steroid-binding $\beta$-globulin, also electrophoresis methods and steps of ion-exchange chromatography may be used for the purification of the steroid-binding $\beta$-globulin. The steroid-binding $\beta$-globulin is adsorbed on basic anion exchangers, for example diaminoethyl exchangers on the basis of cross-linked dextrane, available in the commerce as Diaminoethyl-Sephadex of Messrs. Pharmacia, Uppsala, in a pH-range of from about 4.5 to 9 and can be obtained therefrom by elution with buffer solutions of increasing ion strength. It is of advantage to carry out 2 fractionations on basic ion exchangers, one time by adsorption and fractionated elution of the steroid-binding $\beta$-globulin at a weakly acid pH-value, for example at pH 5.0, and a second time in a neutral to weakly alkaline pH-range, for example at pH 7.0.

Particularly suitable as purification operation is the preparative zone electrophoresis which shows good results when combined with molecular sieving methods.

The zone-electrophoretic process with the aid of carrier substances, too, is advantageously carried out in two different pH-ranges, one time in the alkaline pH-range, for example at pH 8.6, whereby the zone of the $\beta$-range of the plasma proteins is obtained, and the other time in the weakly acid pH-range, for example at pH 5, after which the corresponding zone containing the steroid-binding $\beta$-globulin can be cut out. The sequence of these measures is not compulsory.

If the elution of the protein from the carrier material of the electrophoresis is carried out with a volatile buffer, for example ammonium-hydrogenocarbonate, lyophilization of the product can be carried out directly thereafter.

If plasma is used as starting material for the obtention of steroid-binding $\beta$-globulin, the process may be carried out in the same manner as with placental extract. The pre-precipitation with acridine salts in a weakly acid pH-range, however, is not necessary.

For obtaining the derivative of steroid-binding $\beta$-globulin of the invention, the substance obtained according to the above decribed or comparable purification processes is dissolved in a buffer the pH-value of which corresponds approximately to the optimum conditions of neuraminidase for the separation of neuraminic acid from the substrate by neuraminidase.

Incubation of the steroid-binding $\beta$-globulin with neuraminidase is carried out until the content of neuraminic acid of this protein is reduced to 0.5 $\pm$ 0.5%, thus to less than 1%.

For the treatment of steroid-binding $\beta$-globulin, there may be used glycoprotein N-acetyl-neuraminylhydrolases, which are classified uner EC. 3.2.1.18, so-called neuraminidases, preferably of microbial origin, especially bacterial neuraminidases such as the corresponding enzymes from Vibrio cholerae, pneumococci or Clostridium perfringens. When using a neuraminidase from Vibrio cholerae, the incubation is carried out in a pH-range of from 5 to 7, preferably at pH 5.5, in one of the buffers usually employed in enzymology, advantageously in a buffer solution of trishydroxymethylaminomethane or sodium acetate. In this case, 50-500 units of neuraminidase are added per 100 mg of protein and the incubation is carried out in a temperature range of from 0° to 37° C, preferably at 4° C or at room temperature of 20° C, an incubation for 20 hours at 4° C showing an almost equal reduction of the neuraminic acid content of the protein, i.e. to about 0.5%, as an incubation for 5 hours at 20° C.

As is known to every enzymologist, reactions of this kind may be carried out under the most various conditions so that the same effect, i.e. the removal of neuraminic acid from the steroid-binding $\beta$-globulin and the manufacture of the steroid-binding globulin of the invention can also be carried out at other, lower than the indicated concentrations of neuraminidase with a correspondingly longer incubation period, especially at slightly elevated temperatures and addition of activators of the enzyme.

Some neuraminidases are activated by alkaline earth metal ions. Particularly suitable for the activation of neuraminidase from Vibrio cholerae are, as is known, calcium ions which may be added in the form of water-soluble salts such as calcium chloride in a concentration of 0.1 to 1 mg/ml to the incubation solution. The quantity of the neuraminidase to be used is given by the following definition of the units:

A neuraminidase unit is the quantity of enzyme which is required to set free 1 microgram of N-acetylneuraminic acid from human $\alpha_1$-glycoprotein in a 0.05 molar sodium acetate buffer of pH 5.5 with addition of 9 mg/ml of sodium chloride and 1 mg/ml of calcium chloride within 15 minutes at 37° C (E. Mohr and G. Schramm, Z. Naturf. 15b, page 568, 1960)

The protein derivative which has become more strongly basic by the separation of neuraminic acid than the starting material and therefore shows a weaker bond to basic anion exchangers must be freed from residual impurities and also from any possibly present unchanged starting material by chromatography, for example on a diaminoethyl ion exchanger.

The charge property of the derivative of the invention also permits separation of the impurities by electrophoresis. The eluates containing the steroid-binding β-globulin may be concentrated, dialyzed and lyophilized without showing any signs of denaturation.

In electrophoretic analysis, the steroid-binding globuline shows a uniform line, in ultracentrifugal analysis a uniform band. It reacts with anti-serum against the steroid-binding $β_1$-globulin in the same manner as the original protein. As the original protein, it is binding steroids, in particular testosterone and oestradiol.

The protein derivative prepared according to the invention has an importance in diagnostics insofar as that, on the one hand, the pure antigen, and on the other hand, the specific antiserum obtained by immunization with the pure antigen may be used in methods for the determination of steroid-binding β-globulin. By these methods it is possible to detect and to observe disorders of the steroid status or changes in the content of steroid-binding β-globulin in plasma or in tissues, for example in the course of diseases.

The following Example illustrates the invention.

EXAMPLE

Isolation of the steroid-binding β-globulin from placentas:

10 kg of human placentas in deep-frozen state were comminuted and extracted with 10 liters of a 0.5% sodium chloride solution (1 hour at 5° C). All operations described hereinafter were carried out at 4° C, unless stated otherwise. The buffer solutions used had been combined with 0.05% w/v of sodium azide in order to keep them sterile.

10 Liters of the extraction solution were adjusted to pH 6.0 by means of 20% acetic acid and combined with 1500 ml of a 3% 6,9-diamino-2-ethoxyacridine-lactate solution ("acridine salt solution"). The inactive preprecipitate was separated by centrifugation and rejected. The supernatant was adjusted to pH 8.5 by means of binormal sodium hydroxide solution and precipitated with 3 liters of acridine salt solution. The precipitate which contained the steroid-binding globuline was centrifuged. The liquid supernatant was rejected, the precipitate was suspended in 6 liters of a 5% sodium chloride solution. After removal by centrifugation of the precipitate, the supernatant was combined with solid ammonium sulfate until a saturation of 50%. Thereupon, a precipitate was formed which was separated by centrifugation.

The wet, ammonium sulfate containing paste (250 g) obtained as centrifugation product was dissolved in 1000 ml of water, dialyzed against de-ionized water and, in order to eliminate a part of the accompanying proteins, combined at pH 7.0, a conductivity of 10 mS (adjustment with a 5% sodium chloride solution) and a temperature of 0° C with ethanol until a concentration of 25% was reached. The precipitate formed was removed by centrifugation and rejected; the supernatant, which contained the major quantity of the steroid-binding β-globulin, was dialyzed against water and lyophilized.

Further purification was effected by gel-filtration on Sephadex G-150 (column 20 × 100 cm) using a 0.01 molar trishydroxymethylaminomethane-HCl buffer of pH 7.0.

The proof of the steroid-binding β-globulin in the eluates was carried out immunologically with a specific anti-serum in the gel-diffusion test. The positive fractions (1400 ml) were pooled and, for further purification, adsorbed on a diaminoethyl-Sephadex column (5 × 20 cm).

Elution of the proteins from the diaminoethyl-Sephadex column was effected with 0.01 molar trishydroxymethylaminomethane-HCl buffer using a saline gradient of 0 – 2%. Proof of the steroid-binding β-globulin in the eluate was again carried out immunologically; the fractions containing the steroid-binding β-globulin were combined (900 ml) and precipitated with 35% w/v of ammonium sulfate. The precipitate formed was isolated by centrifugation, dissolved in water, dialyzed first against water and then against a 0,1 molar sodium diethylbarbiturate buffer of pH 8.6. Further separation of the proteins of the dialysate in an electric field was carried out with the apparatus and method described by Heide et al. (1964); as inert carrier material, polyvinyl chloride (Geon X 427), manufacturer Goodrich Chem. Comp., Cleveland/Ohio, U.S.A. and as buffer, a 0.1 molar sodium diethylbarbiturate solution (pH 8.6) was used. The steroid-binding β-globulin migrated in the $β_1$-zone; it was eluted therefrom with a multiple volume of carrier of 0.1% sodium chloride solution and, after removal of the salts by dialysis against water, precipitated with ammonium sulfate (35% w/v). The precipitate was dissolved in 500 ml of a trishydroxymethylaminomethane-HCl buffer of pH 5.0 and dialyzed against a 0.01 molar trishydroxymethylaminomethane-HCl buffer of pH 5.0. Subsequently, the solution was allowed to pass through a diaminoethyl-Sephadex column (5 × 25 cm) which had been equilibrated with the same buffer (pH 5.0). A part of the proteins together with the steroid-binding β-globulin remained adsorbed on the column and was then eluted using a linear sodium chloride gradient of 0 – 2%. The eluates which contained the steroid-binding β-globulin were combined, neutralized and precipitated by the addition of 40% w/v of ammonium sulfate. For the following preparative zone electrophoresis at pH 5.0, Geon X 427 was again used as the carrier material; as buffer, a 0.15 molar sodium acetate solution of pH 5.0 was used. At this pH-value, the steroid-binding β-globulin migrated towards the anode; it was eluted from the corresponding zone with physiological salt solution and, after neutralization of the solution, precipitated by the addition of 40% (w/v) of ammonium sulfate.

Steroid-binding β-globulin was obtained in the same manner from serum, in particular from retroplacental serum. In this case, there were used as starting material for the fractionation according to the above example instead of 10 liters of tissue extract 5 liters of serum which had been diluted with 5 liters of distilled water.

Treatment of the steroid-binding β-globulin with neuraminidase:

In order to separate the neuraminic acid, 150 mg of steroid-binding β-globulin were dissolved in 30 ml of 0.01 molear trishydroxymethylaminomethane buffer of pH 5.5, which contained 0.2 mg of $CaCl_2$ per ml, and incubated with 500 units of neuraminidase from Vibrio cholerae for 20 hours at 4° C. The modified protein was then purified by chromatography on diaminoethyl-Sephadex (2.5 × 20 cm) using a 0.01 molar trishydroxymethylaminomethane-HCl buffer of pH 5.5. The derivative of the steroid-binding β-globulin migrated unhindered through the column, whereas the impurities which still were present in the starting material remained adsorbed. The protein-containing eluate was concentrated in a collodion cartridge (Sartorius-Membranfilter-Gesellschaft), dialyzed thoroughly against water and lyophilized.

We claim:

1. A method for making a modified steroid-binding globulin which comprises treating a steroid-binding $\beta$-globulin starting material having the following properties:
   a. a specific affinity to steroid hormones,
   b. a content of carbohydrates of $12.5 \pm 3\%$, of which are $5.7 \pm 1.2\%$ hexoses, $3.9 \pm 0.8\%$ hexoseamine, calculated as N-acetyl-hexoseamine, $2.9 \pm 0.9\%$ of neuraminic acid, calculated as N-acetyl-neuraminic acid, and $0.1 \pm 0.1\%$ fucose,
   c. the capacity of being precipitated by specific anti-sera,
   d. an electrophoretic mobility corresponding to that of $\beta_1$-globulins,
   e. a sedimentation constant of $4.1 \pm 1.0$ S, measured in a phosphate buffer of pH 6.8,
   f. a sedimentation constant of $1.1 \pm 0.3$ S, measured in a 1% sodium dodecylsulfate solution, and
   g. a molecular weight of $65,000 \pm 5,000$, with neuraminidase, at a pH within the optimum reaction range of the enzyme, until the neuraminic acid content of the steroid-binding $\beta$-globulin starting material is reduced to $0.5 \pm 0.5\%$.

2. The method of claim 1 wherein said neuraminidase is a microbial neuraminidase and said pH is from 5 to 7.

3. The method of claim 1 wherein said steroid-binding $\beta$-globulin starting material is treated with neuraminidase from *Vibrio cholerae* at a pH of 5.5 in a ratio of 50 to 500 units of neuraminidase per 100 mg of protein, at 0° to 20° C. and for 5 to 20 hours, a longer time period within this range being used at lower temperatures within the range specified and a shorter time period within this range being used with higher temperatures within the range specified.

4. A modified steroid-binding globulin made by the method of claim 1, said modified steroid-binding globulin having the following properties:
   a. a specific affinity to steroid hormones,
   b. a content of carbohydrates of $10.4 \pm 2.6\%$, of which are $5.8 \pm 1.2\%$ hexoses, $4.0 \pm 0.8\%$ hexoseamine, calculated as N-acetyl-hexoseamine, $0.5 \pm 0.5\%$ neuraminic acid, calculated as N-acetyl-neuramanic acid, and $0.1 \pm 0.1\%$ fucose,
   c. the capacity of being precipitated by anti-sera which are directed against steroid-binding $\beta$-globulin,
   d. an electrophoretic mobility corresponding to that of gamma-globulin,
   e. a sedimentation constant of $4.1 \pm 1.0$ S, measured in a phosphate buffer at pH 6.8,
   f. a sedimentation constant of $1.1 \pm 0.3$ S, measured in a 1% sodium dodecylsulfate solution, and
   g. a molecular weight of $65,000 \pm 5,000$.

5. In the method for making an anti-serum specific to steroid-binding globulin by immunizing animals with said steroid-binding globulin, the improvement wherein the steroid-binding globulin is the modified steroid-binding globulin of claim 4.

* * * * *